United States Patent [19]
Grabs

[11] Patent Number: 5,091,698
[45] Date of Patent: Feb. 25, 1992

[54] CIRCUIT FOR MEASURING THE INTERNAL RESISTANCE OF A LAMBDA PROBE

[75] Inventor: Manfred Grabs, Wiernsheim, Fed. Rep. of Germany

[73] Assignee: Robert Bosch GmbH, Stuttgart, Fed. Rep. of Germany

[21] Appl. No.: 582,866

[22] PCT Filed: Jan. 10, 1990
[86] PCT No.: PCT/DE90/0006
§ 371 Date: Oct. 4, 1990
§ 102(e) Date: Oct. 4, 1990

[30] Foreign Application Priority Data

Feb. 4, 1989 [DE] Fed. Rep. of Germany ........ 3903314

[51] Int. Cl.[5] ............................................. G01R 27/02
[52] U.S. Cl. ..................... 324/693; 324/713; 324/721; 204/153.16; 204/424; 123/440
[58] Field of Search ............... 324/693, 713, 721, 439, 324/425; 123/440; 204/424, 425, 153.16

[56] References Cited

U.S. PATENT DOCUMENTS

| | | | |
|---|---|---|---|
| 4,419,190 | 12/1983 | Dietz et al. | 204/408 |
| 4,586,476 | 5/1986 | Asayama et al. | 123/440 |
| 4,742,808 | 5/1988 | Blümel et al. | 123/489 |
| 4,759,328 | 7/1988 | Blümel et al. | 123/440 |

Primary Examiner—Kenneth A. Wieder
Assistant Examiner—Glenn W. Brown
Attorney, Agent, or Firm—Walter Ottesen

[57] ABSTRACT

A circuit for measuring the internal resistance of a lambda probe 10 is provided with a junction device 16 for selectively loading the probe. Loading the probe via a junction device affords the advantage that an internal-resistance measurement can be effected in a simple manner within a very wide range of from several ohms up to several megaohms.

8 Claims, 1 Drawing Sheet

CIRCUIT FOR MEASURING THE INTERNAL RESISTANCE OF A LAMBDA PROBE

FIELD OF THE INVENTION

The invention relates to a circuit for measuring the internal resistance of a lambda probe such as is used, in particular, in motor vehicles for measuring the oxygen content in the exhaust gas. It is known that the probe voltage depends greatly on temperature at low temperatures which is why it should only be used for controlling starting at a minimum temperature. Above the minimum temperature, the measurement results are falsified by the internal resistance of the probe unless the measurement is carried out without current and this is not possible in practice.

BACKGROUND OF THE INVENTION

From the U.S. Pat. No. 4,742,808, a circuit for measuring the internal resistance of a lambda probe is known which exhibits a load resistor which is selectively connected in parallel with the probe by means of a switch. A means for measuring the probe voltage measures the probe voltage in the loaded and unloaded state. From the two voltage values and the resistance value of the load resistor, the internal resistance is calculated. As soon as the internal resistance has dropped below a predetermined threshold value, the voltage of the unloaded probe is used for controlling purposes.

For all circuits by means of which the voltage of a lambda probe is detected, the internal resistance of the probe can be used, when the probe is sufficiently warm, to set up a relationship between the measured voltage and the voltage which would actually be measured with a lambda value present in each case when the internal resistance would correspond to that of an operationally warm probe. Thus, the measured voltage can be corrected by means of the internal resistance. It is problematic that when the lambda probe heats up, the internal resistance changes by several powers of ten, namely from a few megohms at 200° C. down to less than 100 ohm at 800° C. If the above-mentioned circuit is to be used to measure the internal resistance in this entire range of resistance values, it is necessary to use several load resistors having quite different resistance values. This is because the order of magnitude of the value of the load resistor must correspond to the internal resistance in order to be able to determine, firstly, when the probe is sufficiently operationally warm and thereafter to obtain reliable measurement results. This leads to the internal resistance first having to be measured roughly by loading it with an arbitrarily selected load resistance. Once the internal resistance has been estimated by means of this measurement, a load resistance must be selected which has a resistance value which is of the order of magnitude of the internal resistance. It is only then that the internal resistance can be reliably measured. As a result, it is necessary during temperature changes of the probe, that is particularly during warmup, to switch time and again from one load resistor to another. The circuit configuration and the measuring process which can be carried out therewith are thus complicated.

The internal resistance of a probe can be measured without any direct-voltage loading within a narrow resistance range by means of a circuit which is described in U.S. Pat. No. 4,419,190. An alternating current of known intensity is sent through the probe and the alternating voltage dropped across the probe is measured. The alternating voltage component is separated from the direct voltage component of the probe and the internal resistance is determined from alternating current and alternating voltage. The measuring process which can be carried out by means of this circuit is thus simple but the circuit complexity is also considerable.

The invention is based on the object of specifying a simple circuit for measuring the internal resistance of a lambda probe.

SUMMARY OF THE INVENTION

The circuit according to the invention is characterized by a junction device which can be selectively connected in parallel with the lambda probe with the aid of a switch. A means for measuring the probe voltage in the loaded and unloaded state is provided.

This circuit has the advantage that in the loaded state a voltage occurs which changes with the logarithm of the internal resistance. In an illustrative embodiment, a voltage of 800 mV in the loaded state was measured when loaded with a transistor in the presence of a rich mixture with 100 ohm internal resistance (about 800° C.). The measured voltage changed by about 70 mV per power of ten of increase in internal resistance so that a voltage of 420 mV was picked up with an internal resistance of about 1 megohm (about 280° C.).

When using a junction device instead of an ohmic resistance as load resistance component, it is problematic that the reverse current included in the measurement result is highly temperature-dependent. This temperature dependence does not become noticeable in a disturbing manner only if it has been ensured that only slight temperature fluctuations occur at the circuit, for example by accommodating the latter in a control device the temperature of which is controlled.

If the circuit is subject to temperature changes, it is of advantage to arrange the junction device in good thermal contact with a temperature sensing element. Advantageously, further components of a control device are also arranged in good thermal contact with this temperature sensing element so that it is possible to compensate for temperature-dependent characteristics of these components with the aid of the temperature sensing. This measure can also be taken with great advantage when the temperature-dependent components in the control device do not include a junction device for a circuit for measuring the internal resistance of a lambda probe.

A transistor is of particular advantage as junction device. This is because the reverse current in transistors having the same current gain is essentially independent of component characteristics which, for example, does not apply to diodes. Independently of the transistor used, the same measurement results are thus obtained with the same probe voltage and same internal resistance in each case with a predetermined type. In addition, the highly temperature-dependent reverse current can then be easily measured by detecting the current at a second transistor which is in good thermal contact with the loading transistor. If the circuit has two constant current sources, the second transistor can also be used for measuring the thermal voltage.

Reverse current and thermal voltage can be measured not only with the aid of a second transistor but also with the aid of the loading transistor. However, a greater number of switches is then necessary. The additional transistor is more cost-effective than additional switches and the measuring process becomes simpler without continuously required switching-over.

DESCRIPTION OF THE PREFERRED EMBODIMENTS OF THE INVENTION

Figure 1:
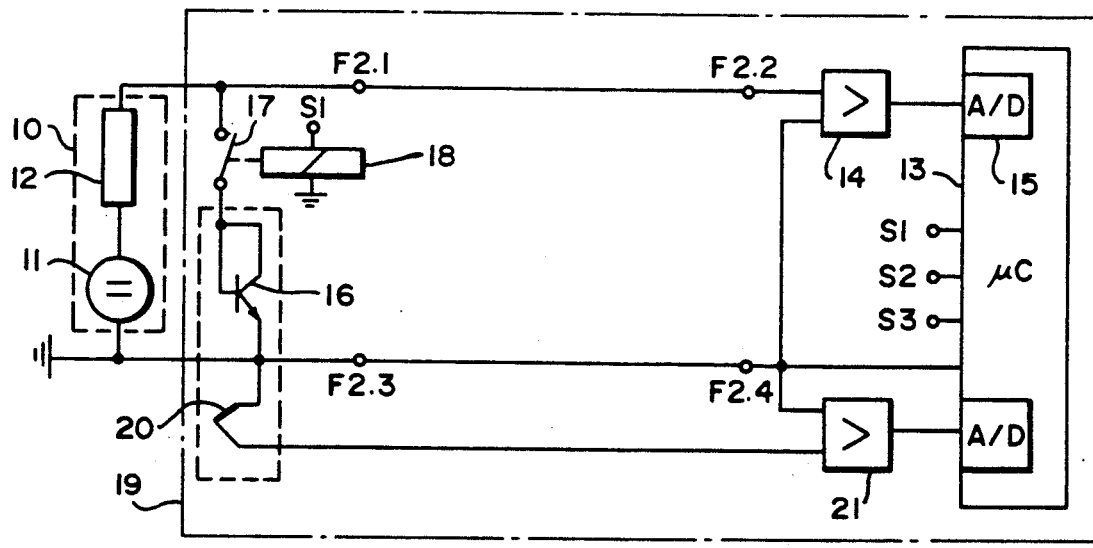
FIG. 1 is a circuit diagram of a circuit for measuring the internal resistance of a lambda probe with the aid of a loading transistor; and, FIG. 2 is a circuit diagram corresponding to that of FIG. 1 but supplemented by a circuit section for measuring reverse current and thermal voltage.

The circuit according to FIG. 1 shows, among other things, a lambda probe 10 by means of its equivalent circuit which consists of a probe voltage source 11 and a probe resistance 12. The probe voltage source 11 outputs the probe voltage US. The probe resistance 12 exhibits an internal resistance RS which greatly depends on the temperature of the probe. It is, for example, about 100 ohm at 800° C. and about 1 megohm at 280° C. The probe voltage US is detected by a means for measuring the probe voltage which is configured as microcomputer 13. The probe voltage, amplified by a probe voltage amplifier 14, is converted by an A/D converter 15 into a digital signal which can be processed by the microcomputer 13. The probe voltage US fluctuates between a few millivolts with a warm probe, which measures a lean mixture, and about 900 mV with a warm probe in a rich mixture. This voltage is amplified by a factor of 5 by the probe voltage amplifier 14. In this application, however, reference is always made to non-amplified voltages.

To load the lambda probe 10, a load transistor 16 is present which can be connected in parallel with the probe 10 with the aid of a load switch 17. The load switch 17 is activated by a load switch relay 18. This relay receives its control signal from an output S1 of the microcomputer 13. It is pointed out that a practical embodiment does not contain a load switching relay with mechanical switch but a switching transistor. In FIG. 1 and also in FIG. 2, however, all switches are shown as mechanical switches with relays and not as transistors so that the transistors which are of importance for the operation of the resistance measuring circuit are particularly clearly emphasized.

As soon as the load transistor 16 is connected in parallel with the lambda probe 10, a load current IL flows through the circuit thus formed. This load current IL generates a voltage drop across the probe resistance 12 of a value of RS×IL which is opposite to the probe voltage US. Accordingly, the voltage UL at load is:

$$UL = US - RS \times IL.$$

The internal resistance of the probe is calculated from the above as:

$$RS = (US - UL)/IL \qquad (1)$$

It is pointed out that the voltage UL occurring when the lambda probe 10 is loaded occurs at the probe voltage amplifier 14 when the load switch 17 is closed, that is when it happens to be in the other position from that shown in FIG. 1. Because the position is different in FIG. 1, the probe voltage US with unloaded probe is drawn in there at the input of the probe voltage amplifier 14.

Equation (1) contains the load current as unknown quantity. The following holds true for the latter:

$$IL = ISP \times exp(UL/UT) \qquad (2)$$

wherein:
 ISP = reverse current (component-independent transistor constant) and
 UT = thermal voltage (kT/eO)

Equation (2) inserted in equation (1) yields the internal resistance RS:

$$RS = (1/ISP) \times (US - UL) \times exp(-UL/UT) \qquad (3)$$

It will be initially assumed that the load transistor 16 is arranged in a control device 19 the temperature of which is controlled to a constant value. The control device 19 is shown by a dot-dashed line in FIG. 1. The values of reverse current ISP and thermal voltage UT are known with a known constant temperature. The internal resistance is then obtained from equation (3) with the measured values of the voltage US of the probe in the unloaded state and the voltage UL of the probe in the loaded state.

With the circuit according to FIG. 1, that is using an npn transistor the base and collector of which are connected together as load transistor 16, the following values resulted for the measured voltage UL in the loaded state with a probe idling voltage of 1 V:

| RS | 100 Ω | 1 kΩ | 10 kΩ | 100 kΩ | 1 MΩ |
|---|---|---|---|---|---|
| UL | 700 mV | 630 mV | 560 mV | 490 mV | 420 mV |

This example shows that the measurement values clearly differ from one another and that they are located within a range which can be easily covered. The internal resistance can thus be measured accurately and with little expenditure over its entire range of several powers of ten.

In practice, it is an exception for the temperature of a control device to be controlled. Normally, the temperature of the control device is not known and changes within wide limits. However, the thermal voltage UT then also fluctuates slightly and the reverse current ISP fluctuates very greatly. To be able to measure the temperature of the load transistor 16 for the subsequent calculation of reverse current and thermal voltage, a thermocouple 20 is provided in the embodiment according to FIG. 1 which is in good thermally conductive contact with the load transistor 16. This good thermally conductive contact is indicated by a dashed line which encloses the load transistor 16 and the thermocouple 20. The voltage of the thermocouple 20 is supplied to the microcomputer 13 after amplification by a thermal-voltage amplifier 21. The microcomputer calculates the internal resistance from equation (3), inserting the value which is valid for the temperature measured in each case for the reverse current ISP and the thermal voltage UT.

It is advantageous if not only the load transistor 16 is brought into good thermally conductive contact with the thermocouple 20 or another temperature sensing element but if this measure is also taken for other electronic components in the control device which have temperature-dependent characteristics. It has up till now been attempted to counter temperature-dependent characteristics of control device components by means of special compensation circuits or by selecting components having a low variation with temperature. For example, a special circuit is used to generate a reference voltage which has as little temperature dependence as possible. This circuit can be considerably simplified if the temperature of temperature-dependent components is known and then temperature influences are compensated mathematically by means of the microcomputer present in each control device. The measure of arranging a temperature sensing element in good thermal contact with electronic components which have temperature-dependent characteristics is thus advantageous not only in conjunction with a circuit for measuring the internal resistance of a lambda probe. Instead, this measure can also be used in control devices which do not have a circuit for measuring the internal resistance of a lambda probe.

Figure 2:
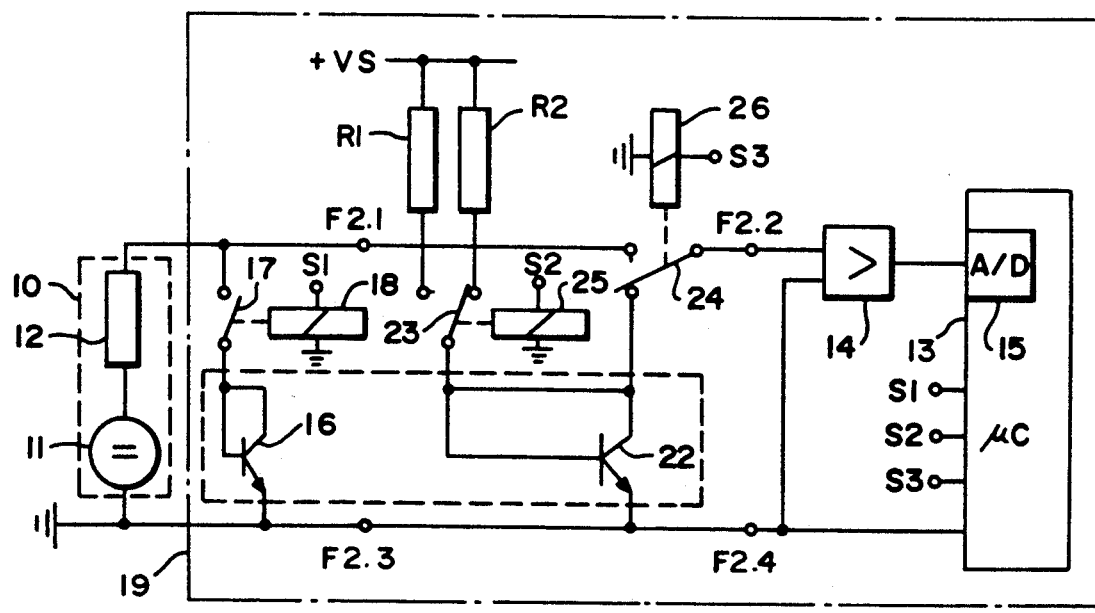

The circuit according to FIG. 2 only differs from that according to FIG. 1 in that the thermocouple 20 and the associated thermal voltage amplifier 21 are not present and that, instead, a circuit section used for compensating temperature effects is present between the points F2.1-F2.4 drawn in FIG. 1. This circuit section has a compensation transistor 22, a compensation switch 23, a change-over switch 24 and two constant current sources which are formed by two resistors R1 and R2 which are connected to the supply voltage +VS of, for example, 5 V. The compensation switch 23 is controlled by a compensation switch relay 25 and the change-over switch 24 is controlled by a change-over switch relay 26. These receive their operating signals via terminals S2 and S3, respectively, on the microcomputer 13. The load transistor 16 itself could also be used as compensation transistor 22 but this would require even more switches than are required by the illustrative embodiment according to FIG. 2. It is pointed out that in the embodiment according to FIG. 2, the load switching relay 18 can easily also switch the compensation switch 23. The practical embodiment contains as switches two transistors the base of which is jointly driven.

Using the circuit section just explained, the reverse current ISP can be calculated utilizing equation (2). For this purpose, a constant load current IL of value IR1 is set, that is, a current having an intensity which is determined by the values of supply voltage VS and first resistor R1. The voltage dropping across the transistor is designated as UR1. From equation (2), the known load current IR1 and the measured voltage UR1 are used to calculate the reverse current ISP as follows:

$$ISP = IR1 \times exp(-UR1/UT) \qquad (4)$$

If the value for the reverse current ISP, calculated with the aid of equation (4), is inserted into equation (3), the latter now only contains one quantity which is not accurately known, namely the thermal voltage UT. The value of the thermal voltage UT can be set to a mean value such as the applicable, for example, to 20° C., for measurements which do not require too high an accuracy. For more accurate measurements, however, the following further procedure is adopted.

After the voltage drop UR2 across the compensation transistor 22 has been measured with a constant current IR1 flowing therethrough, a voltage UR2 is also measured which drops across the transistor 22 while a constant second current IR2 flows therethrough. An equation corresponding to equation (4) is then applicable, namely:

$$ISP = IR2 \times exp(-UR2/UT) \qquad (4')$$

From equations (4) and (4'), the thermal voltage UT is then calculated as follows:

$$UT = (UR2 - UR1)/LN(UR2/UR1) \qquad (5)$$

The value of the thermal voltage UT calculated from equation (5) can be directly inserted into equation (3). In addition, the value of the thermal voltage UT is inserted into equation (4) and the value of the reverse voltage ISP, which has been accurately determined as a result, is used for evaluating equation (3). The internal resistance RS can thus be accurately determined without the temperature of the control device 19 itself being known.

Instead of a transistor, a different junction device can also be used as loading component, particularly a diode. However, diodes have the disadvantage that the reverse current therein is component-dependent.

I claim:

1. A circuit for measuring the internal resistance of a lambda probe having a probe voltage source for outputting a probe voltage, the circuit comprising:
    a junction device;
    a switch selectively movable between a first position wherein said junction device is disconnected from said probe and a second position for connecting the junction device in parallel with the probe thereby applying said junction device as a load to said probe; and,
    measuring means connected to the probe for making a first measurement of the probe voltage when said junction device is disconnected from said probe and a second measurement of the probe voltage when said junction device is connected across said probe.

2. The circuit of claim 1, wherein said junction device is a load transistor.

3. The circuit of claim 2, wherein said load transistor is an npn transistor having a base and a collector; and, said base and said collector being connected together.

4. The circuit of claim 2, further comprising: a compensation transistor arranged in thermal contact with said junction device for measuring the temperature-dependent reverse current of said junction device.

5. The circuit of claim 4, further comprising: a first constant current source for generating a first constant current flow having a first current intensity through said compensation transistor.

6. The circuit of claim 5, further comprising: a second constant current source for generating a second constant current flow having a second known current intensity through said compensation transistor; and, ancillary switching means for alternately connecting said first and second constant current sources to said compensation transistor for calculating the thermal voltage UT from the first and second voltages UR1 and UR2 dropped across the compensation transistor for the two current intensities from the equation:

$$UT = (UR2 - UR1)/LN(UR2/UR1).$$

7. The circuit of claim 1, further comprising a temperature sensing element arranged in thermal contact with said junction device for measuring the temperature of said junction device.

8. The circuit of claim 7, wherein said temperature sensing element is arranged in a control device in thermal contact with electronic components which have temperature-dependent characteristics.

* * * * *